United States Patent
Kim et al.

(10) Patent No.: US 12,419,961 B2
(45) Date of Patent: Sep. 23, 2025

(54) DOCETAXEL-ACONITIC ANHYDRIDE CONJUGATE EXHIBITING ANTI-TUMOR ACTIVITY WITHOUT IN VIVO TOXICITY

(71) Applicant: CNPharm Co., Ltd., Seoul (KR)

(72) Inventors: Hojun Kim, Seoul (KR); Geun-Woo Jin, Seoul (KR)

(73) Assignee: CNPharm Co., Ltd., Seoul (KR)

( * ) Notice: Subject to any disclaimer, the term of this patent is extended or adjusted under 35 U.S.C. 154(b) by 764 days.

(21) Appl. No.: 17/719,718

(22) Filed: Apr. 13, 2022

(65) Prior Publication Data

US 2022/0323589 A1 Oct. 13, 2022

Related U.S. Application Data

(63) Continuation-in-part of application No. 17/320,592, filed on May 14, 2021, now abandoned.

(60) Provisional application No. 63/174,175, filed on Apr. 13, 2021.

(51) Int. Cl.
*A61K 47/54* (2017.01)
*C07D 407/12* (2006.01)

(52) U.S. Cl.
CPC .......... *A61K 47/545* (2017.08); *C07D 407/12* (2013.01)

(58) Field of Classification Search
CPC .............................. C07D 407/12; A61K 47/545
See application file for complete search history.

(56) References Cited

U.S. PATENT DOCUMENTS

| | | | |
|---|---|---|---|
| 2007/0292384 A1 | 12/2007 | Song et al. | |
| 2017/0037193 A1 | 2/2017 | Song | |
| 2018/0360978 A1 | 12/2018 | Blume-Jensen et al. | |
| 2021/0315998 A1* | 10/2021 | Kim | C07D 323/02 |

OTHER PUBLICATIONS

"Pubchem CID 148124", Jun. 24, 2005 (Jun. 24, 2005), entire document, especially p. 3, compound listed.
Emami et al, "Novel pH-triggered biochompatible polymeric micelles based on heparin-alpha-tocopherol conjugate for intracellular delivery of docetaxel in breast cancer", Jan. 4, 2020 (Jan. 4, 2020), Pharmaceutical Development and Technology, vol. 25, Issue 4, pp. 1-46, entire document, especially p. 4, para 1; p. 6, para 2; p. 7, para 1.
Yan et al., "Co-delivery of docetaxel and curcumin prodrug via dual-targeted nanoparticles with synergistic antitumor activity against prostate cancer", Biomedicine & Pharmacotherapy, 88 (2017), pp. 374-383, entire document, especially p. 374, col. 1, para 1, col. 2, para 2; p. 375, col. 1, para 3; Figures 1,4.

* cited by examiner

*Primary Examiner* — James D. Anderson
(74) *Attorney, Agent, or Firm* — Procopio, Cory Hargreaves & Savitch LLP

(57) ABSTRACT

Synthesizing a docetaxel-aconitic anhydride conjugate using docetaxel, including: mixing aconitic anhydride with a chlorinating reagent to produce a first mixture; dissolving the first mixture in an organic solvent to produce a dissolved mixture; stirring the dissolved mixture; evaporating the organic solvent from the dissolved mixture to produce a second mixture; washing the second mixture with an impurity remover to remove impurities and to produce an aconitic anhydride chloride solution; and mixing the docetaxel with the produced aconitic anhydride chloride solution to produce the docetaxel-aconitic anhydride conjugate.

13 Claims, 14 Drawing Sheets

132

130

134

136

138

A1Tx

DOCETAXEL-ACONITIC ANHYDRIDE CONJUGATE EXHIBITING ANTI-TUMOR ACTIVITY WITHOUT IN VIVO TOXICITY

CROSS-REFERENCE TO RELATED APPLICATIONS

This application is a continuation-in-part application of co-pending U.S. patent application Ser. No. 17/320,592 (filed May 14, 2021). This application also claims the benefit of priority under 35 U.S.C. § 119(e) of U.S. Provisional Patent Application No. 63/174,175, filed Apr. 13, 2021. The disclosures of the above-referenced applications are incorporated herein by reference.

BACKGROUND

Field

The present disclosure relates to docetaxel-aconitic anhydride conjugate, and more specifically, to docetaxel-aconitic anhydride conjugate exhibiting good anti-cancer activity while having substantially less in vivo toxicity.

Background

Pancreatic cancer is a notoriously lethal cancer. At diagnosis, 10-20% of patients are considered as candidates for a curative surgery. Approximately 80% of pancreatic cancer patients are diagnosed at a point when the disease is metastatic and the median overall survival rate is less than six months. The first anti-cancer drug used in the pancreatic cancer was 5-fluorouracil (5-FU) which provided an improvement in the median overall survival rate compared to supportive care (6 moths vs. 2.5 months). When compared to 5-FU, gemcitabine showed a better survival rate (5.65 months vs. 4.41 months). However, the effect on the survival is still disappointing.

To overcome this limited outcome achieved with the chemotherapy agents mentioned above, other agents have been tested for advanced pancreatic cancer. Among others, taxanes were tested as a single agent or in combination with others in pancreatic cancer since they showed promising results in other solid tumors such as breast cancer, NSCLC, advanced squamous cell carcinoma, head and neck cancer, and stomach cancer. The FDA-approved taxanes include paclitaxel and docetaxel. The mechanism of action consists of tubulin binding and stabilizing microtubule assembly, which is a key process for an inhibition of microtubule de-polymerization that is responsible for the cell division and proliferation. Among them, docetaxel (DTX) has been known to be better than paclitaxel in clinical efficacy due to its higher affinity toward tubulin. However, DTX has been known to have many disadvantages, in particular, severe side effects such as weight loss, neutropenia, and hypersensitivity reaction.

SUMMARY

The present disclosure provides for synthesizing docetaxel-aconitic anhydride conjugate (A3Tx) which shows anti-cancer activity without causing toxicity problems represented by weight loss. The present disclosure also provides for synthesizing A2Tx and A1Tx1.

BRIEF DESCRIPTION OF THE DRAWINGS

The details of the present disclosure, both as to its structure and operation, may be gleaned in part by study of the appended drawings, in which like reference numerals refer to like parts, and in which.

DETAILED DESCRIPTION

Figure 1A:
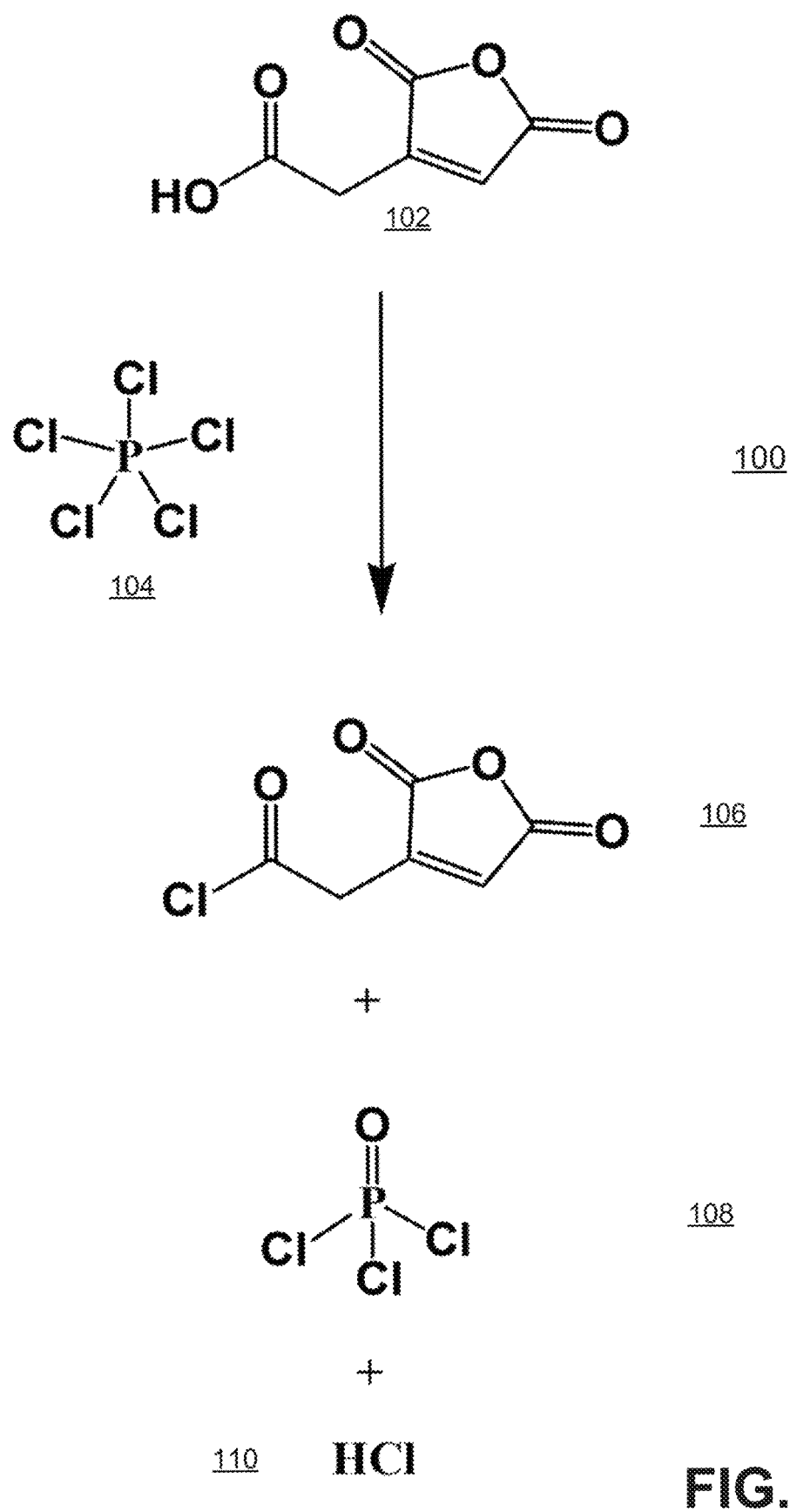
FIGS. 1A and 1B show a process for synthesizing A3Tx linking docetaxel and aconitic anhydride in accordance with one implementation of the present disclosure.

As mentioned above, to overcome the limited success achieved with the chemotherapy agents, other agents have been tested for advanced pancreatic cancer. Among others, taxanes were tested as a single agent or in combination with others in pancreatic cancer. The FDA-approved taxanes include paclitaxel and docetaxel (DTX). However, as noted above, DTX has been known to have many disadvantages including severe side effects such as weight loss, neutropenia, and hypersensitivity reaction.

Some study results have indicated that the chemical structure modification of taxane is a promising way of improving toxicity, compared to its native form. Further, the study results have indicated that the chemical modification affects anti-cancer activity against cancer cells, making it a potentially viable approach in advancing taxanes.

Certain implementations of the present disclosure include chemical modifications made at three different functional sites, OH group at positions C-2' (HO-C-2'), C-7 (HO-C-7), and C-10 (HO-C-10), which are made possible by the presence of three hydroxyl groups on the DTX molecule. The studies show the benefit of modifying these functional moieties. The modified DTX exhibited greater potency than DTX in multidrug-resistant cancer cells, because of its weaker binding affinity to P-glycoprotein, a drug efflux pump that plays an important role in reducing intracellular concentrations of anti-cancer drugs. For the modification, aconitic anhydride was employed, which has been used in the field of biomaterials for the functional group modification and formation of bio-degradable linker. Aconitic anhydride does not cause any toxicity since it can be metabolized into aconitic acid, an intermediate of the TCA cycle localized in the mitochondrial matrix. Accordingly, a new taxane, docetaxel-aconitic anhydride conjugate (A3Tx) (i.e., hydroxyl-modified DTX with aconitic anhydride) has been synthesized through the chemical conjugation of three hydroxyl groups (HO-C-2', 7, and 10) on docetaxel with aconitic anhydride. The cell viability assay result showed higher toxicity of A3Tx towards pancreatic cancer cells (PANC-1) over normal ones (L929). That is, the cell experiment has shown that A3Tx has higher toxicity toward cancer cell line (PANC-1), while it has lower cytotoxicity toward normal cell line (L929). The in vivo studies with BALB/c mice bearing PANC-1 pancreatic carcinoma tumors revealed that A3TX significantly delays tumor growth. However, no weight loss was observed in animal models treated with A3Tx during the tested period.

In one implementation, anticancer drug for the conjugation of aconitic anhydride is not limited to docetaxel. The anticancer drug may be one selected from the below-listed compounds (including a hydroxyl or primary amine group), but is not limited to: (a) Taxane-based drugs such as paclitaxel or docetaxel, colchicine analogs (microtubule inhibitors), and in addition to those, a naturally-derived substance that inhibits a division of cells by binding to tubulin present in a cell; (b) Platinum compounds such as cisplatin, carboplatin, nedaplatin, and other similar compounds; (c) Deoxyribonucleic Acid (DNA) intercalating agent such as mitoxantrone; (d) Anthracycline-based drugs such as doxorubicin, idarubicin, and other than those, drugs which block cell growth and division by directly binding to the DNA to destroy the molecule itself and damage the same or double helix structure of the DNA; (e) The DNA synthesis inhibitors such as methotrexate (MTX), and other than those, drugs that interfere with the action by competitively binding with normal metabolites to the enzymes of biosynthesizing purine and pyrimidine, which are constituents of DNA and RNA; (f) Topoisomerase I inhibitor such as camptothecin, and other similar inhibitors; (g) Endocytosis inhibitor such as hydroxychloroquine, and other similar inhibitors; (h) Protease inhibitor such as nafamostat, and other similar inhibitors; and (i) Drugs which were proven as having anti-virus effect against reterovirus such as niclosamide, cyclosporine, perhexiline maleate, loperamide, mefloquine, amodiaquine, proscillaridin, phenazopyridine, digitoxin, penfluridol, clomiphene, toremifene, digoxin, hexachlorophene, hydroxyprogesterone, thioridazine, salinomycin, quinacrine, eltrombopag, cepharanthine, ciclesonide, oxyclozanide, LDK378, dihydrogambogic acid, osimertinib (AZD-9291), isopomiferin, anidulafungin (LY303366), osajin, lusutrombopag, isoosajin, gilteritinib, berbamine, ebastine, tetrandrine, abemaciclib (USAN), ivacaftor, bazedoxifene, mequitazine, triparanol, droloxifene, dronedarone, lopinavir, favipiravir, atazanavir, and other similar drugs.

In another implementation, the conjugating chemical is not limited to aconitic anhydride and may be one selected from the compounds listed below, but is not limited to: (a) Aconitic anhydride and aconitic acid derived compounds; (b) Succinic anhydride and succinic acid derived compounds; (c) Glutaric anhydride and glutaric acid derived compounds; (d) Citric anhydride and citric acid derived compounds; (e) Maleic acid derivative such as 1-methyl-2-(20-carboxyethyl) maleic anhydride (MCM), carboxylate dimethyl maleic anhydride (CDM), and other similar derivatives; and (f) Other anhydrides of polyhydric organic acids and derivatives thereof.

In another implementation, the conjugation method is not limited to acyl chloride formation and may be one selected from the chemical reactions listed below, but is not limited to: (a) esterification by using coupling reagents such as Carbodiimide (DCC, DIC, EDC HCl), BOP, PyBOP, PyAOP, PyBrOP, BOP-Cl, HATU, HBTU, HCTU, TATU, TBTU. (b) amidation by using coupling reagents such as Carbodiimide (DCC, DIC, EDC HCl), BOP, PyBOP, PyAOP, PyBrOP, BOP-Cl, HATU, HBTU, HCTU, TATU, TBTU.

In one implementation, the pharmaceutical compositions can be developed as drugs through following formulations.
  (a) In the cases of intravascular and subcutaneous injections: (1) Micelle formulation using amphipathic polymers such as polyethylene glycol poly-lactide-co-glycolide (PEG-PLGA) and polyethylene glycol-b-poly L-lysine (PEG-PLL); (2) Formulation using surfactants such as Tween 80, and organic solvent such as ethanol; (3) Sustained releasing formulation through binding of pH sensitive or degradable polymers.
  (b) In the case of oral administration: (1) Formulations containing enteric coating agents including polymers such as Eudragit, PEG or poloxamers); (2) Formulations containing polysaccharide-based substances such as starch and dextran; (3) Sustained-release formulation through a pH-sensitive or degradable polymer mixture; and (4) The following substances which can be used as additives to make the above formulation. trietyl citrate, hydroxypropyl methylcellulose (HPMC), cellulose acetate succinate, carboxyvinyl polymer such as carbomer, cellulose acetate phthalate, carboxymethyl cellulose, cellulose acetate phthalate, hydroxypropyl cellulos, ethyl cellulose, methyl cellulose, polyvinyl acetate phthalate, polyvinyl alcohol (PVA)
  (c) In order to control a release of drugs and prevent a degradation, depending on the route of administration, there are plasticizer, solubilizing agent, sweetener agent, gelling agent, bonding agent, hardener, surfactant, anticaking agent, brightener, flavors enhancer, base, sugar coating agent, bulking agent for freeze-drying, isotonic agent, effervescent agent, desiccant, release-modifying agent, antimicrobial preservative, anti-adherent, filler, diluent, disintegrant, acidifying agent, oxidizer, osmotic regulator, sustained release modifying agent, cleanser, antifoaming agent, humectant, stabilizing agent, alkalizing agent, antioxidant, suspending agent, glidant agent, pH modifier, enteric coating agent such as Eudragit.

In one implementation, a list of diseases to be treated with the pharmaceutical composition alone or through a mixture of two or more including the following:
  (a) Diseases caused by bacterial and viral infections including: (1) Infectious diseases including viral infection, malaria infection, and bacterial infection; virus disease including Epstein Barr virus (EBV), hepatitis B virus, hepatitis C virus, HIV, HTLV 1, varicella-zoster virus (VZV), and human papilloma virus (HPV); and (2) Corona virus infections such as SARS-CoV1 and SARS-CoV2, other retrovirus infections;
  (b) Inflammatory disease including: (1) Vascular restenosis; and (2) Inflammatory diseases including autoimmune diseases, pancreatitis, glomerular nephritis, myocardial infarction, and psoriasis, allergic asthma, atopic dermatitis (eczema), and atopic disease (atopy) including allergic rhinitis; (3) cell mediated hypersensitivity, including allergic contact dermatitis and hypersensitivity pneumonitis; (4) rheumatic diseases including Systemic Lupus Erythematosus (SLE), rheumatoid arthritis, juvenile arthritis, Sjogren's syndrome, scleroderma, polymyostitis, Ankylosing Spondylitis and psoriatic arthritis; (5) diabetes, autoimmune thyroid diseases, brain diseases, including dementia, Parkinson's disease, Alzheimer's disease, and other autoimmune diseases; (6) viral diseases including Epstein Barr virus (EBV), hepatitis B virus, hepatitis C virus, HIV, HTLV 1, varicella-zoster virus (VZV), and human papilloma virus (HPV); and (7) degenerative diseases including prion infection, Creutzfeldt-Jakob disease, and arthritis; and (c) Malignant tumor such as cancer including fibrosarcoma, myxosarcoma, liposarcoma, chondrosarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonic carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma, and carcinoma created in breast, prostate, kidney, bladder, or colon tissue; tumor diseases appearing in adipose tissue, such as adipose cell tumors, e.g., lipoma, fibrolipoma, lipoblastoma, lipomatosis, hibemoma, hemangioma, and/or liposarcoma.

Figure 1B:
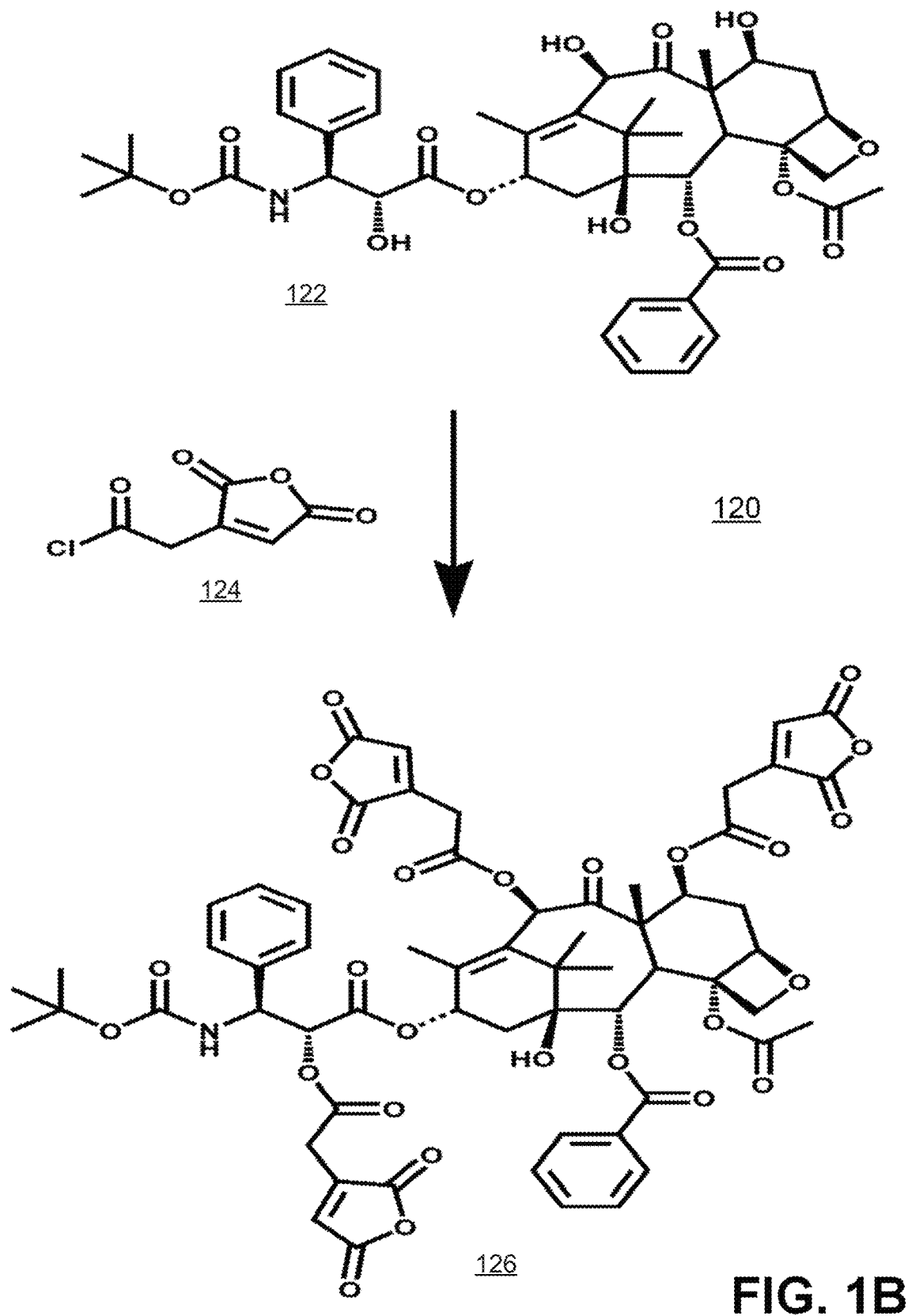

FIGS. 1A and 1B show a process 100, 120 for synthesizing A3Tx 126 linking docetaxel 122 and aconitic anhydride 102 in accordance with one implementation of the present disclosure. In the illustrated implementation of FIGS. 1A and 1B, the process 100, 120 of synthesizing the A3Tx 126 includes following steps.

(a) Mix or acylate aconitic anhydride 102 with chlorinating reagent such as phosphorus pentachloride ($PCl_5$) 104 to prepare for acyl chloride derivative of aconitic anhydride (i.e., aconitic anhydride chloride (AACl) 106) producing by-products including $POCl_3$ 108 and HCl 110.

(b) Dissolve the mixture from step (a) above in methylene chloride.

(c) Stir the dissolved mixture for approximately 1 to 2 hours.

(d) Evaporate methylene chloride (e.g., using rotary evaporator at room temperature) from the dissolved mixture to produce a second mixture.

(e) Wash the second mixture with cyclohexane to remove certain impurities based on the solubility of the solvent and to produce the aconitic anhydride chloride (AACl) solution 106. In one implementation, the second mixture is dispersed in cyclohexane, and the cyclohexane is then centrifuged and decanted to remove the impurities.

(f) Mix or react docetaxel 122 and the produced AACl solution 124 to produce a docetaxel-aconitic anhydride conjugate, A3Tx 126. In one implementation, docetaxel 122 is tri-substituted with aconitic anhydride 102 through the chemical reaction with AACl solution 124. Through this single step, the aconitic anhydride 102 is directly conjugated to the hydroxyl moieties of docetaxel 122. In one implementation, the conjugate is produced by adding the produced AACl solution in methylene chloride or tetrahydrofuran (THF). In one implementation, the molar ratio between docetaxel and AACl is ranged from 1:3 to 1:10.

Figure 1C:
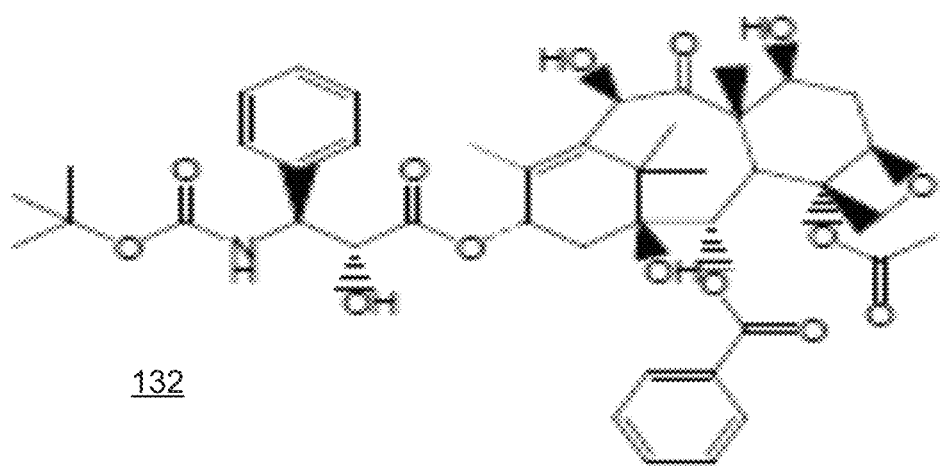
FIG. 1C show an example process for synthesizing A1Tx in accordance with one implementation of the present disclosure.
Figure 1C:
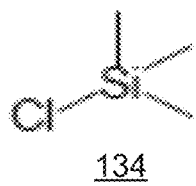
Figure 1C:
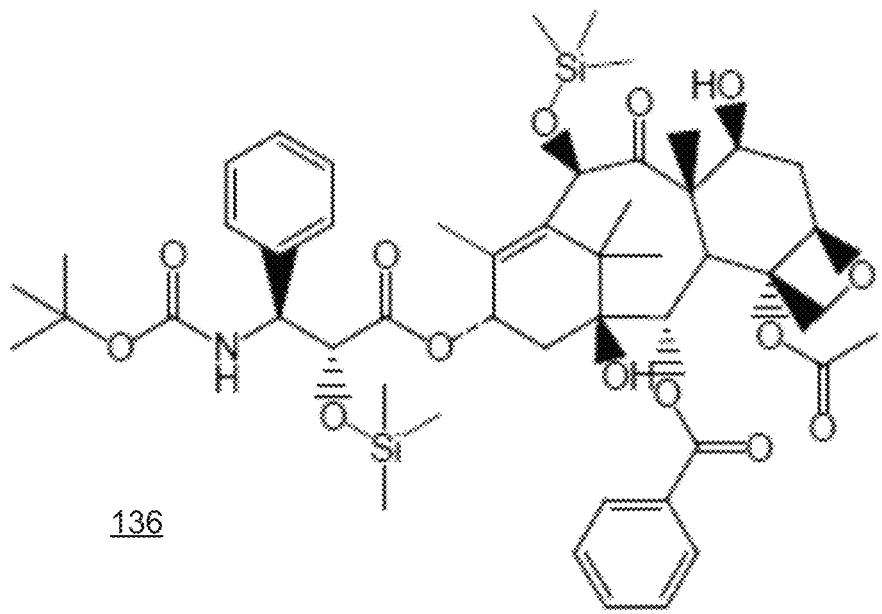
Figure 1C:
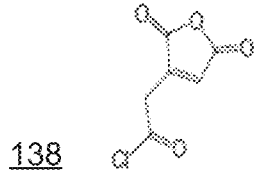
Figure 1C:
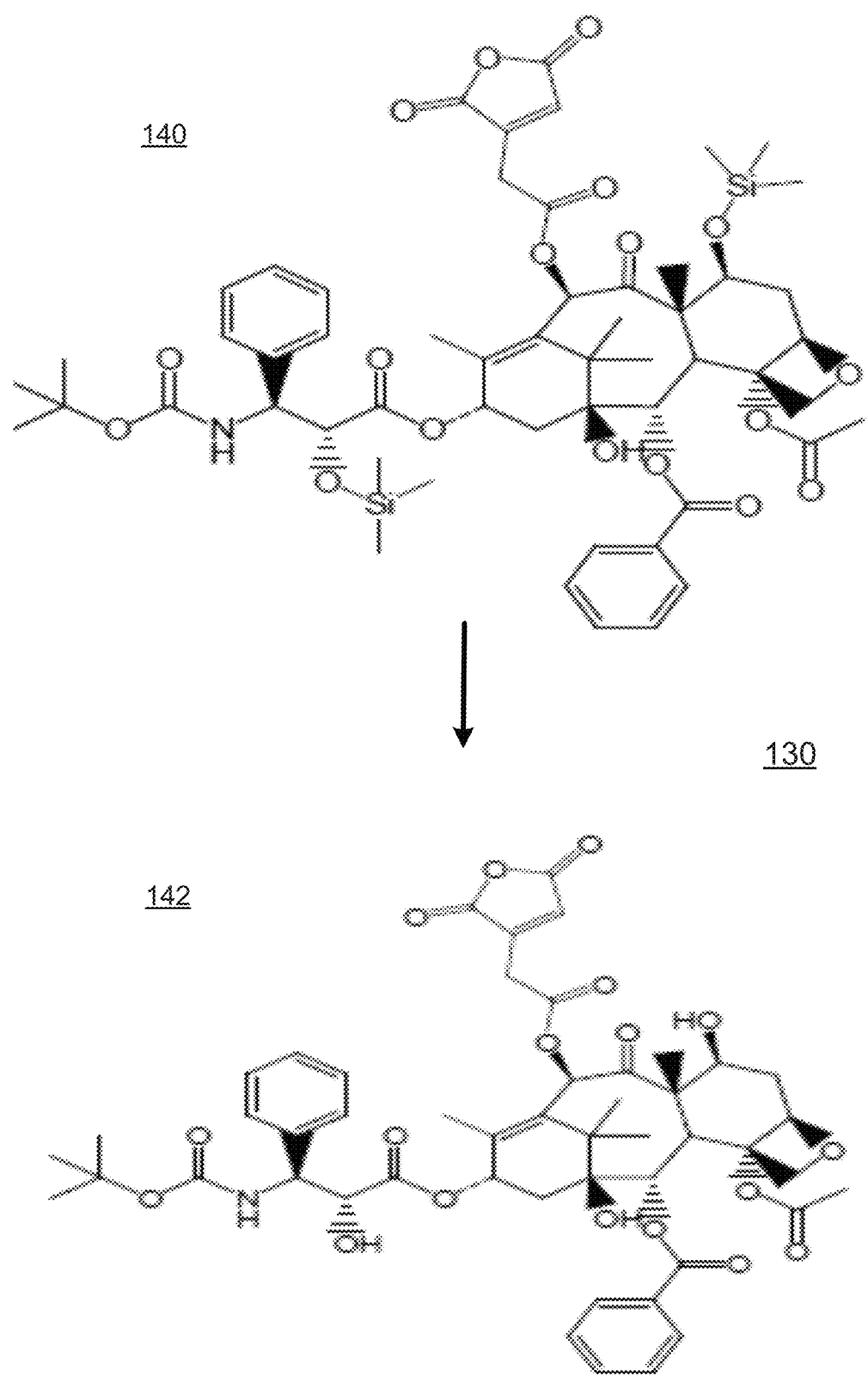

FIG. 1C show an example process 130 for synthesizing A1Tx in accordance with one implementation of the present disclosure. In the illustrated implementation of FIG. 1C, the process 130 of synthesizing A1Tx includes following steps. Substantially similar process can be used to synthesize A2Tx.

In the illustrated implementation of FIG. 1C, the DTX precursor is synthesized by trimethylsilyl (TMS) protection/deprotection and cis-aconitic anhydride conjugation. Cis-aconitic anhydride was activated by acyl chloride formation using PC15. Cis-aconitic anhydride (6.0 g, 38.4 mmol) and PC15 (8.0 g, 38.4 mmol) were dissolved in 10 mL of methylene chloride. The mixture was stirred for 2 hours in room temperature. Then, the solvent was evaporated and washed with cyclohexane to obtain cis-aconitic anhydride chloride (AACl). The hydroxyl group of DTX 132 was protected using trimethylsilyl chloride (TMSC1) 134. DTX (5.0 g, 6.2 mmol) and TMSC1 (0.8 mL, 10.8 mmol) were dissolved in anhydrous MC (40 mL) and stirred in −6° C. After 2 hr, the product was purified by washing with ether. Then, the protected DTX (5.0 g) 136 was mixed with AACl (1.1 g) 138 in THF (5 mL) as solvent. The mixture was stirred at −15° C. for 1 hr. The product was washed with ether and dried to prepare for the disilyl-protected A1Tx 140. For the deprotection of TMS, 0.2N HCl was trated and reacted at −6° C. After 2 hr, DTX precursor 142 was produced by several times of washing with isopropyl ether.

Figure 7A:
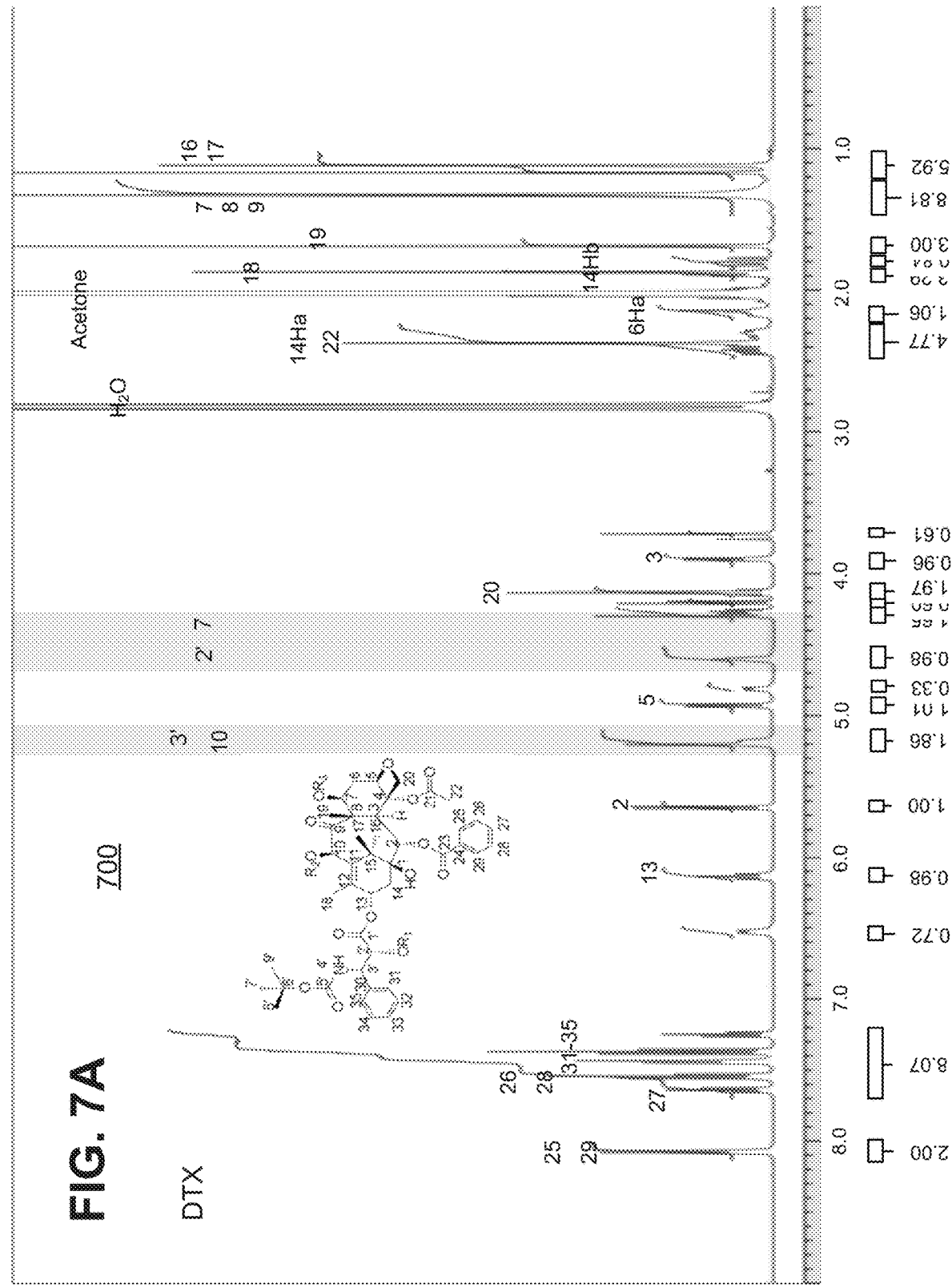
FIGS. 7A and 7B show the proton nuclear magnetic resonance (proton NMR, hydrogen-1 NMR, or 1H-NMR) analysis result of the A1Tx.
Figure 7B:
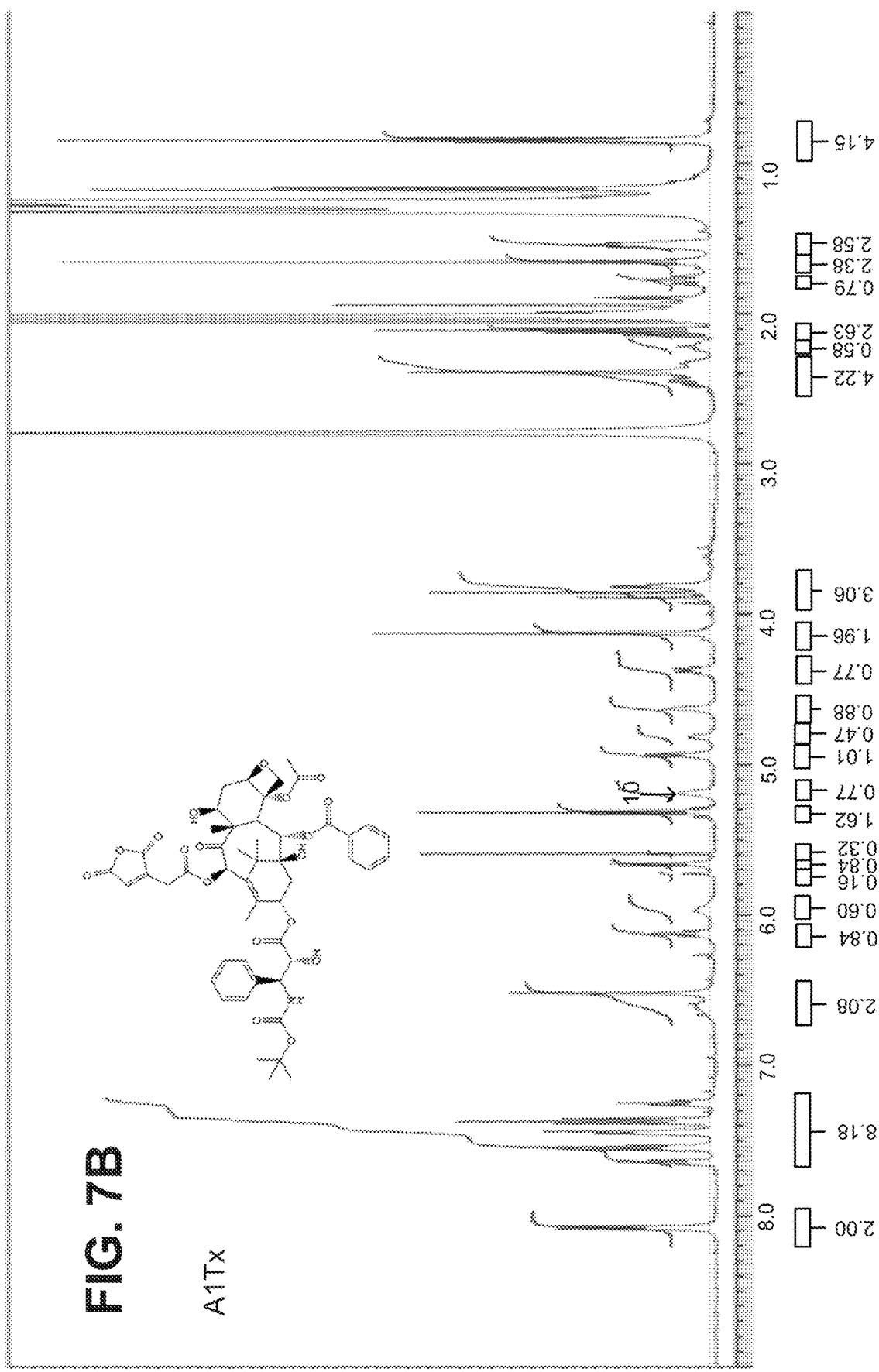

FIGS. 7A and 7B show the proton nuclear magnetic resonance (proton NMR, hydrogen-1 NMR, or 1H-NMR) analysis result 700, 710 of the A1Tx. In the illustrated implementation of FIGS. 7A and 7B, it is confirmed that the peak (5.2 ppm) corresponding to C10-OH is reduced such that A1Tx is structurally conjugated with an aconitic anhydride to C10-OH.

Figure 8:
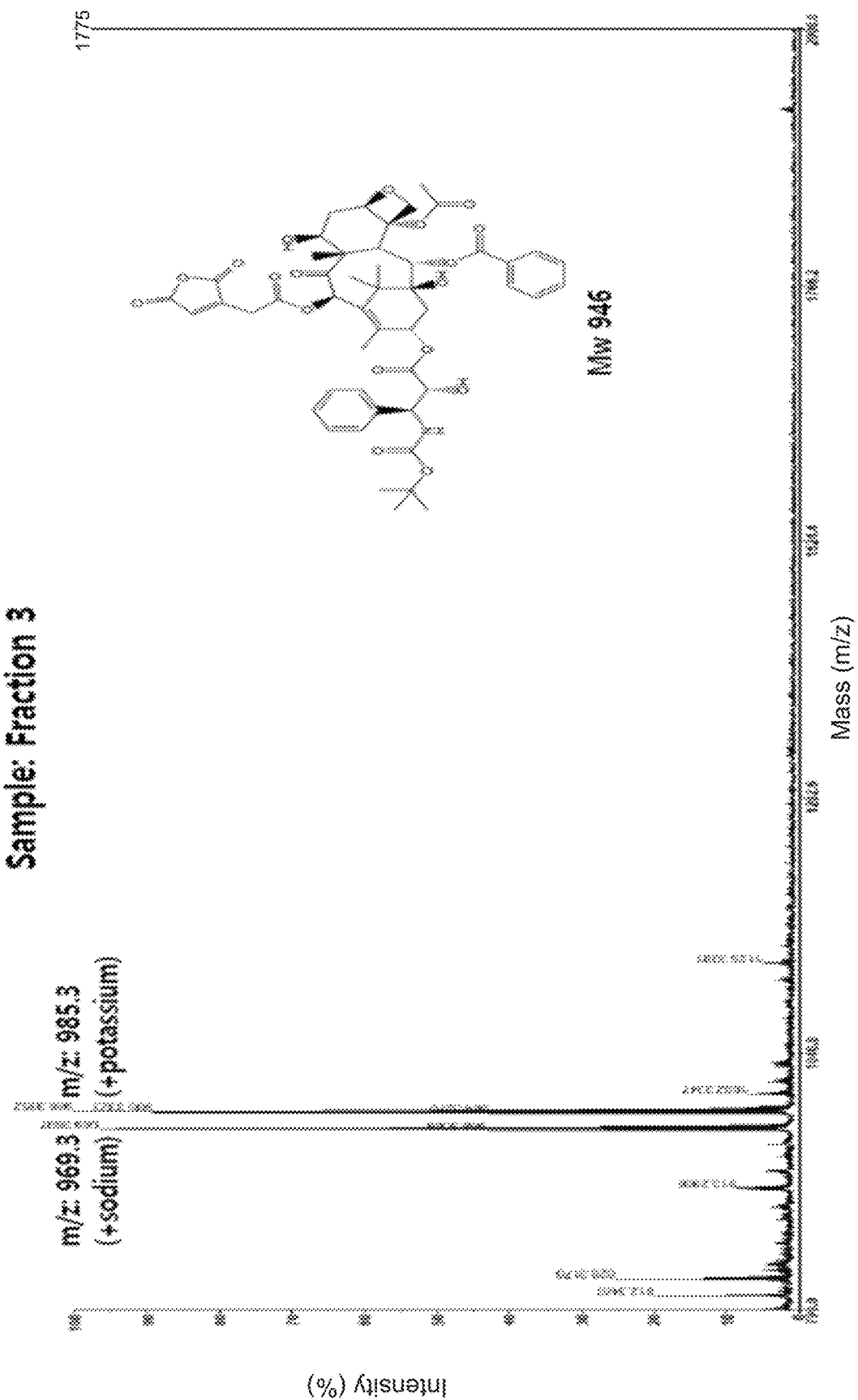
FIG. 8 shows the molecular weight of A1Tx using matrix assisted laser desorption ionization-time of flight (MALDI-TOF) mass spectrometry.

FIG. 8 shows the molecular weight of A1Tx using matrix assisted laser desorption ionization-time of flight (MALDI-TOF) mass spectrometry. In the illustrated implementation of FIG. 8, it is observed that A1Tx is properly synthesized. This result is confirmed using the MALDI-TOF mass spectrometry of 985.3 and 969.3 corresponding to the potassium and sodium adduct of 946, which are theoretical molecular weights of A1Tx.

Figure 9:
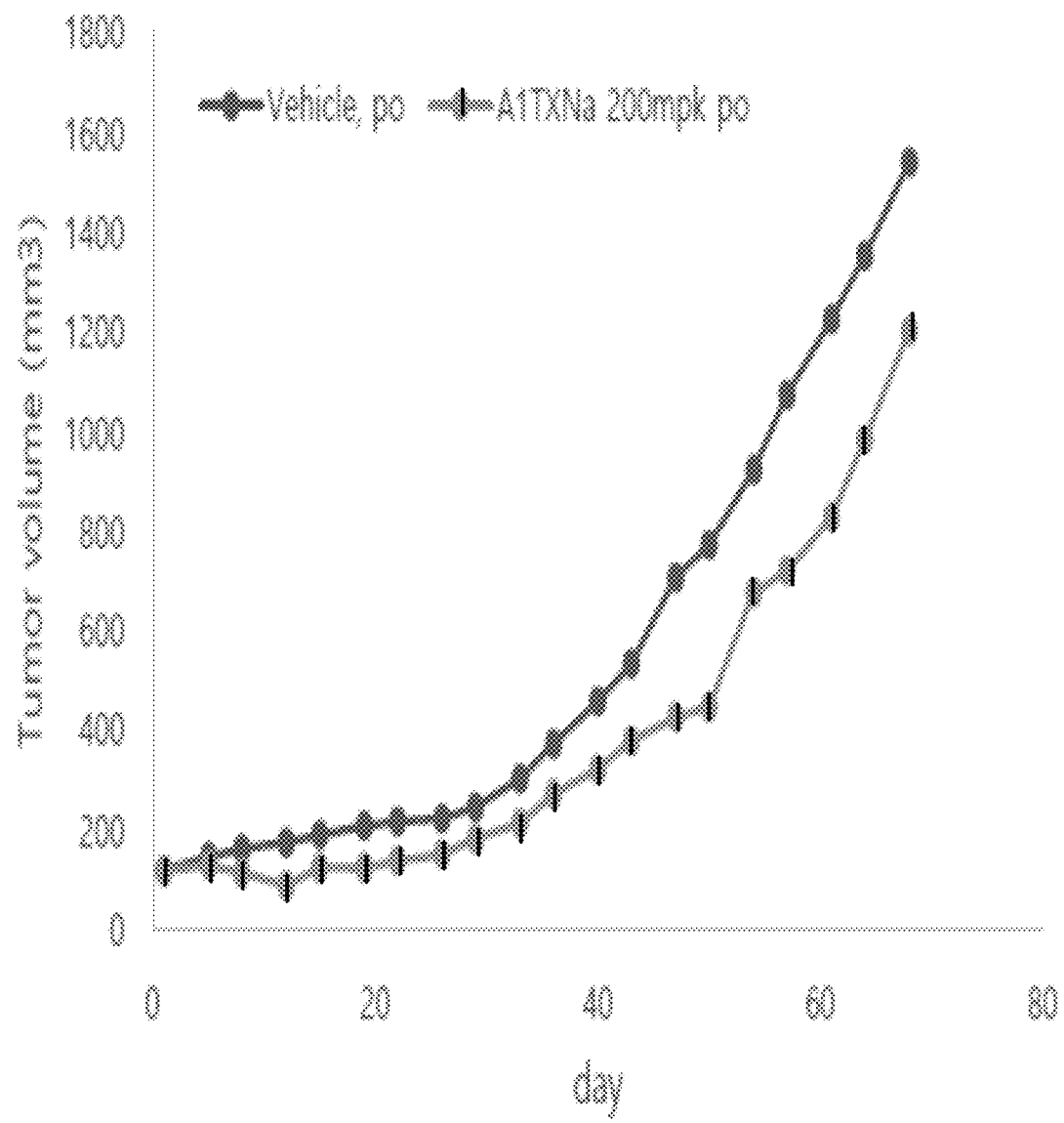
FIG. 9 shows the test results of the anti-cancer effects of A1Tx.

FIG. 9 shows the test results of the anti-cancer effects of A1Tx. In the test, A1Tx was orally administered twice a day (200 mg/kg) for 2 weeks to rats.

Figure 2:
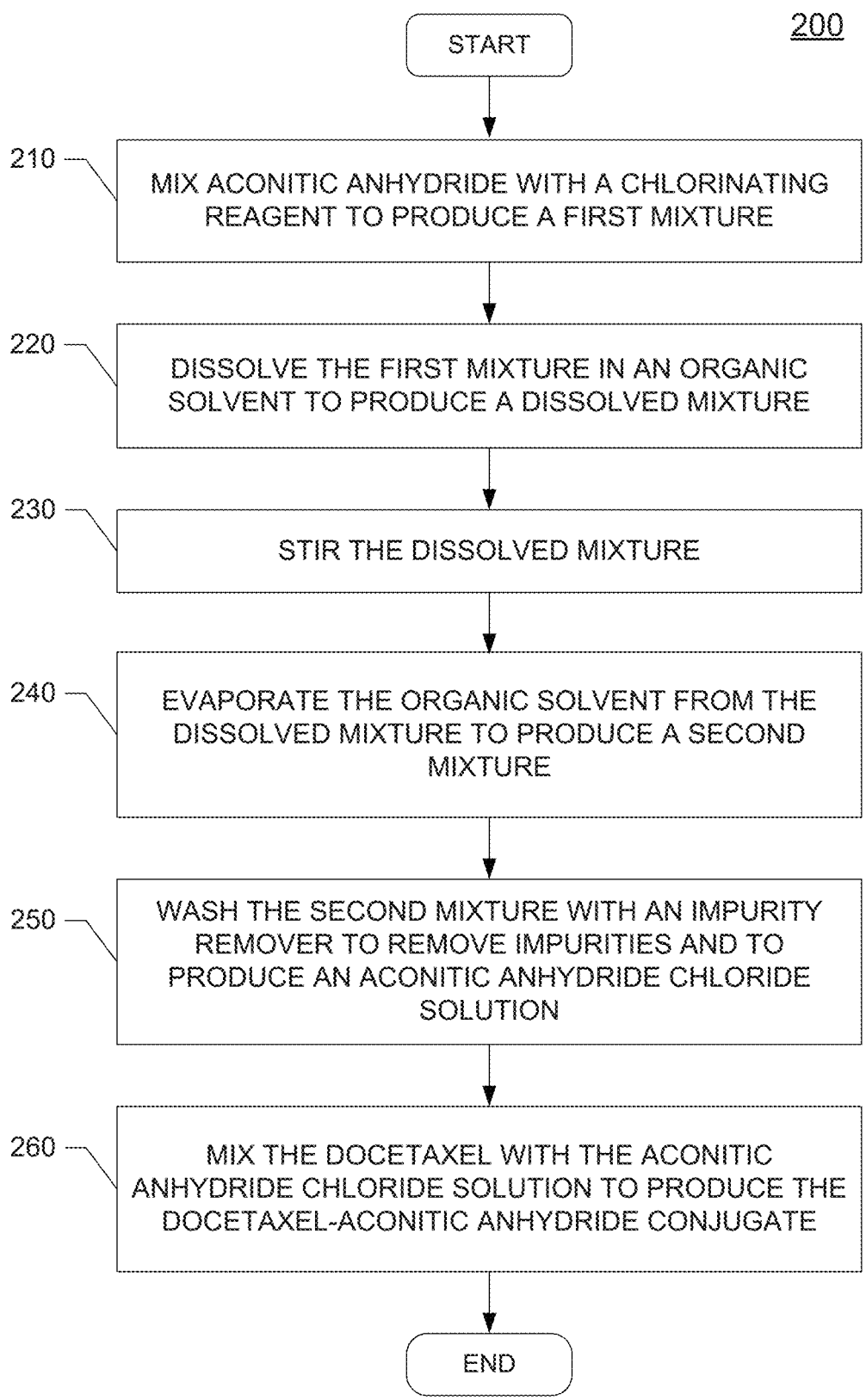
FIG. 2 is a flow diagram of a method for synthesizing docetaxel-aconitic anhydride conjugate in accordance with one implementation of the present disclosure.

FIG. 2 is a flow diagram of a method 200 for synthesizing docetaxel-aconitic anhydride conjugate in accordance with one implementation of the present disclosure. The method 200 initiates with mixing or acylating, at step 210, aconitic anhydride with a chlorinating reagent (e.g., phosphorus pentachloride ($PCl_5$) to prepare for acyl chloride derivative of aconitic anhydride (i.e., aconitic anhydride chloride (AACl)) to produce a first mixture. The first mixture is dissolved, at step 220, in an organic solvent (e.g., methylene chloride). The dissolved mixture is then stirred, at step 230, for approximately 1 to 2 hours, and the organic solvent is evaporated (e.g., using rotary evaporator at room temperature), at step 240, to produce a second mixture. The second mixture is washed, at step 250, with impurity remover (e.g., cyclohexane) to remove certain impurities based on the solubility of the solvent and to produce the aconitic anhydride chloride (AACl) solution. In one implementation, the second mixture is dispersed in cyclohexane, and the cyclohexane is then centrifuged and decanted to remove the impurities.

The docetaxel and the produced AACl solution are mixed or reacted, at step 260, to produce a docetaxel-aconitic anhydride conjugate (see 126 in FIG. 1B). In one implementation, docetaxel is tri-substituted with aconitic anhydride through the chemical reaction with AACl solution. The aconitic anhydride is directly conjugated to the hydroxyl moieties of docetaxel by this step. In one implementation, the conjugate is produced by adding the produced AACl solution in methylene chloride or THF. In one implementation, the molar ratio between docetaxel and AACl is ranged from 1:3 to 1:10.

Figure 3A:
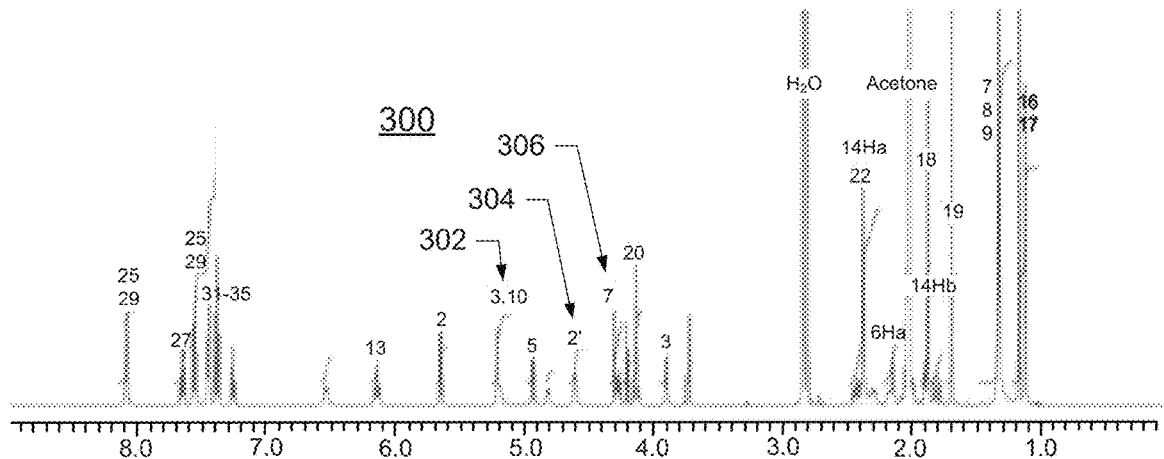
FIGS. 3A and 3B show the proton nuclear magnetic resonance (proton NMR, hydrogen-1 NMR, or $^1$H-NMR) analysis result of the A3Tx synthesized by linking aconitic anhydride and docetaxel in accordance with one implementation of the present disclosure.
Figure 3B:
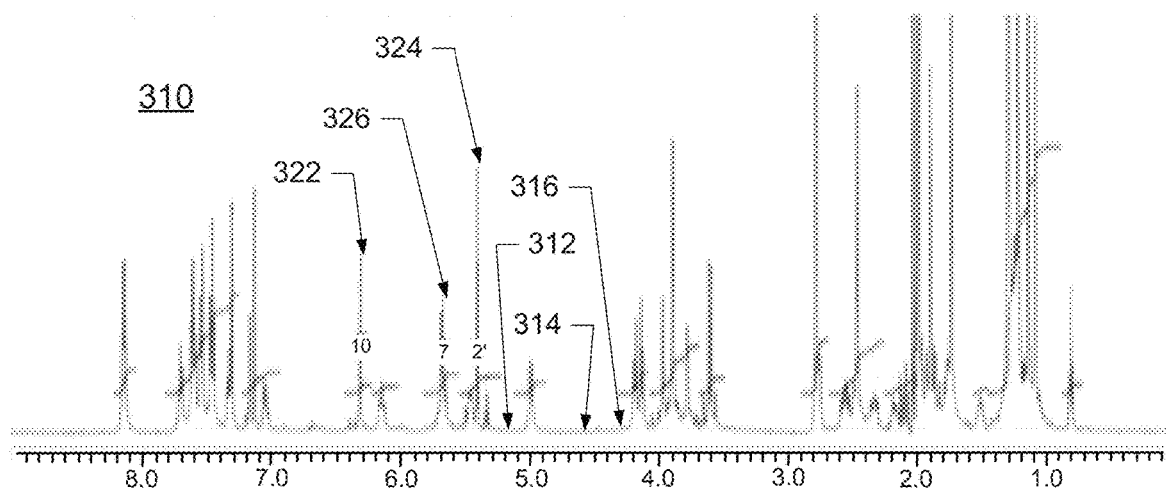

FIGS. 3A and 3B show the proton nuclear magnetic resonance (proton NMR, hydrogen-1 NMR, or $^1$H-NMR) analysis result 300, 310 of the A3Tx synthesized by linking aconitic anhydride and docetaxel. The $^1$H-NMR result confirms that aconitic anhydride is conjugated at three hydroxyl moieties on docetaxel.

Graph 300 of FIG. 3A shows the proton connected to C-10 (302), the proton connected to C-2' (304), and the proton connected to C-7 (306).

Graph 310 of FIG. 3B shows the $^1$H chemical shift for the hydrogens connected to C-2' (4.62 ppm), C-7 (4.28 ppm) and C-10 (5.20 ppm) atoms resonated at down-field of $^1$H-NMR spectra due to the conjugation. For example, the conjugation of aconitic anhydride to the OH group at the C-10 atom (HO-C-10) is verified by the absence of the peak at 5.20 ppm (312) and its shift to a new peak at 6.52 ppm (322). The peak at 4.62 ppm (314) (HO-C-2) was not detected and reallocated to a new peak at 5.44 ppm (324), verifying the conjugation of aconitic anhydride to OH group at the C-2 atom of DTX. The conjugation of aconitic anhydride to HO-C-7 position is demonstrated by the disappearance of the peak at 4.28 ppm (316) (HO-C-7) and a shift to a new peak at 5.68 ppm (326).

Figure 3C:
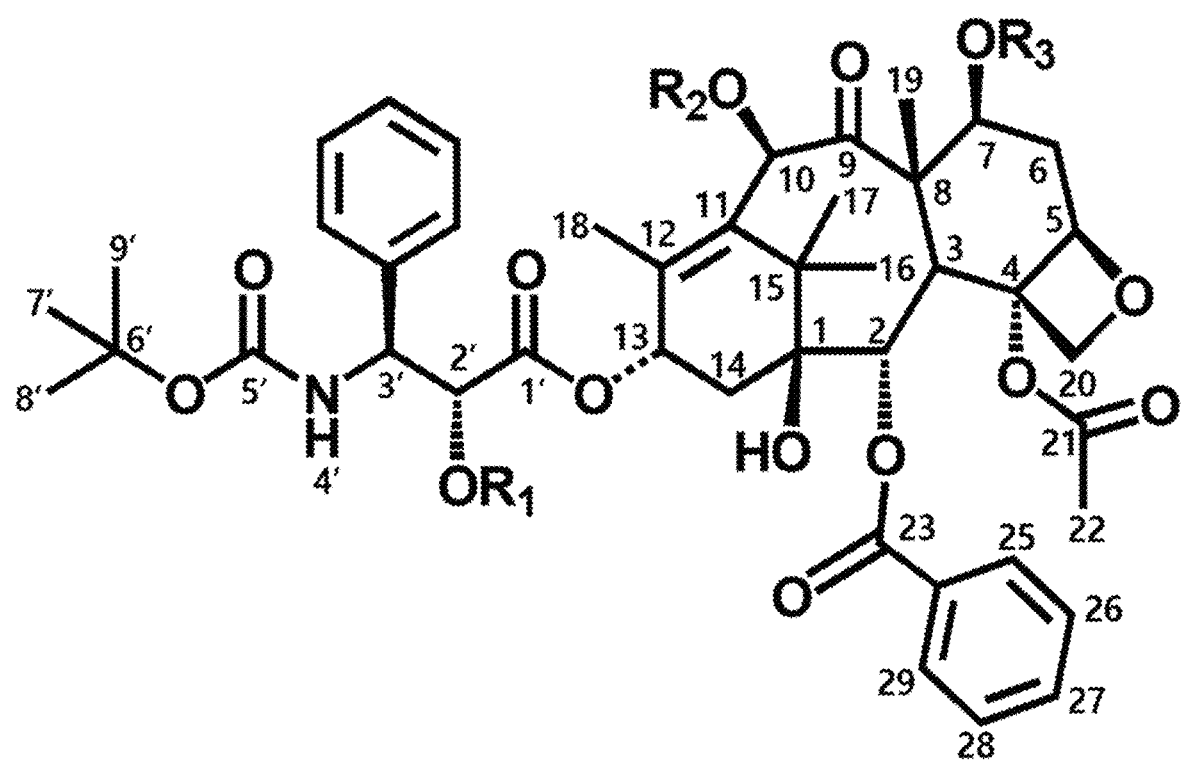
FIG. 3C shows the docetaxel-aconitic anhydride conjugate with position numbers inserted.

FIG. 3C shows the docetaxel-aconitic anhydride conjugate with position numbers inserted. In FIG. 3C, $R_1=R_2=R_3=$aconitic anhydride having the following formula:

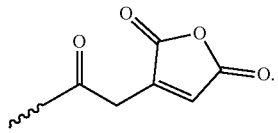

Figure 4:
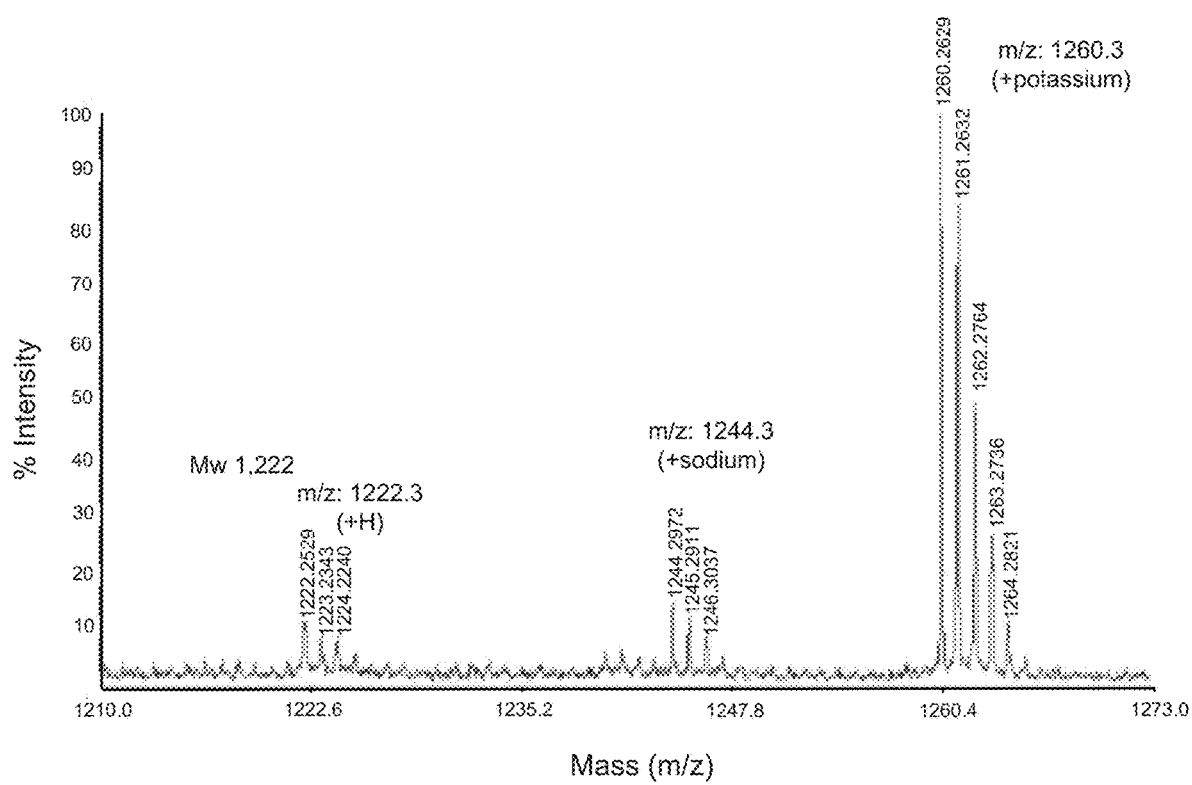
FIG. 4 shows the molecular weight of A3Tx in accordance with one implementation of the present disclosure.

FIG. 4 shows the molecular weight of A3Tx. The result shows that the molecular weight of the synthesized A3Tx is 1221.3, which agrees with the theoretical molecular weight value of A3Tx.

Figure 5A:
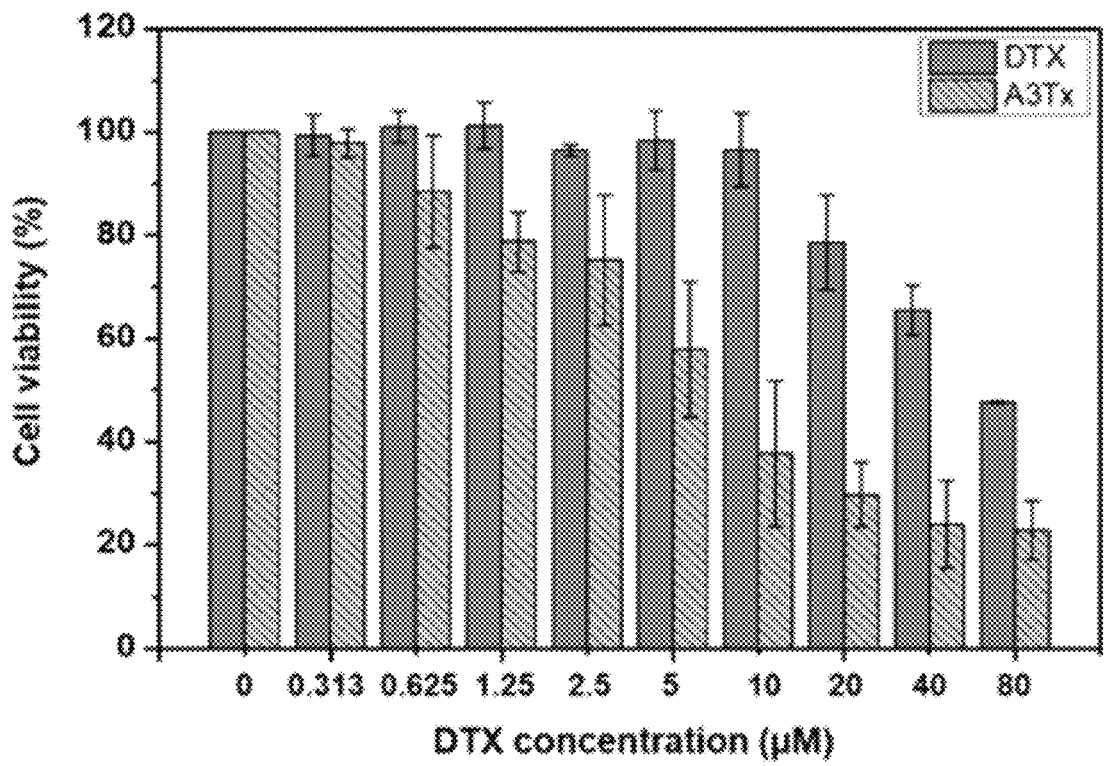
FIG. 5A shows the effective cancer cell killing effect of A3Tx on PANC-1 in accordance with one implementation of the present disclosure.
Figure 5B:
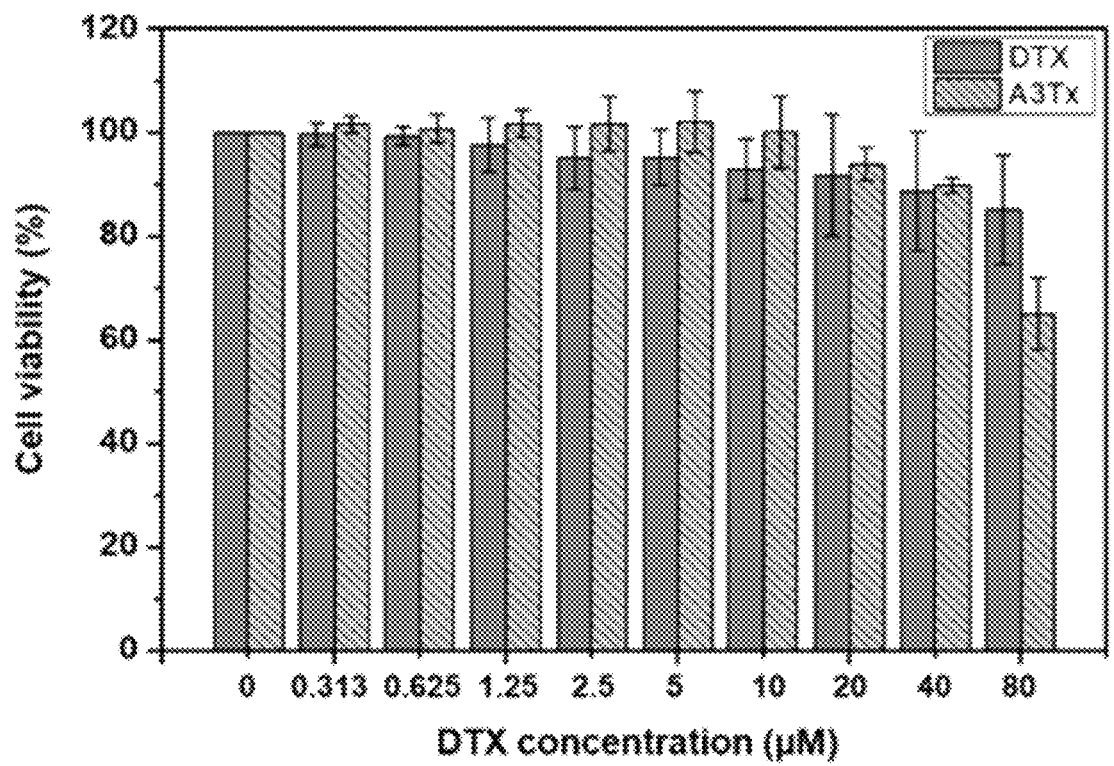
FIG. 5B shows the effective cancer cell killing effect of A3Tx on L929 cell lines in accordance with one implementation of the present disclosure.

FIG. 5A shows the effective cancer cell killing effect of A3Tx on PANC-1. FIG. 5B shows the effective cancer cell killing effect of A3Tx on L929 cell lines. In FIG. 5A, A3Tx shows higher cytotoxicity than DTX against cancer cell line, PANC-1. However, in FIG. 5B, low cytotoxicity was observed in DTX or A3Tx-treated L929 cell line. The results indicate an increase in cytotoxicity of A3Tx against pancreatic cancer cells. In contrast, A3Tx is found to be less active and inefficient at inhibiting cell growth in normal mouse fibroblast cell line (L929), which indicates A3Tx exhibits less cytotoxicity toward normal cells.

Figure 6A:
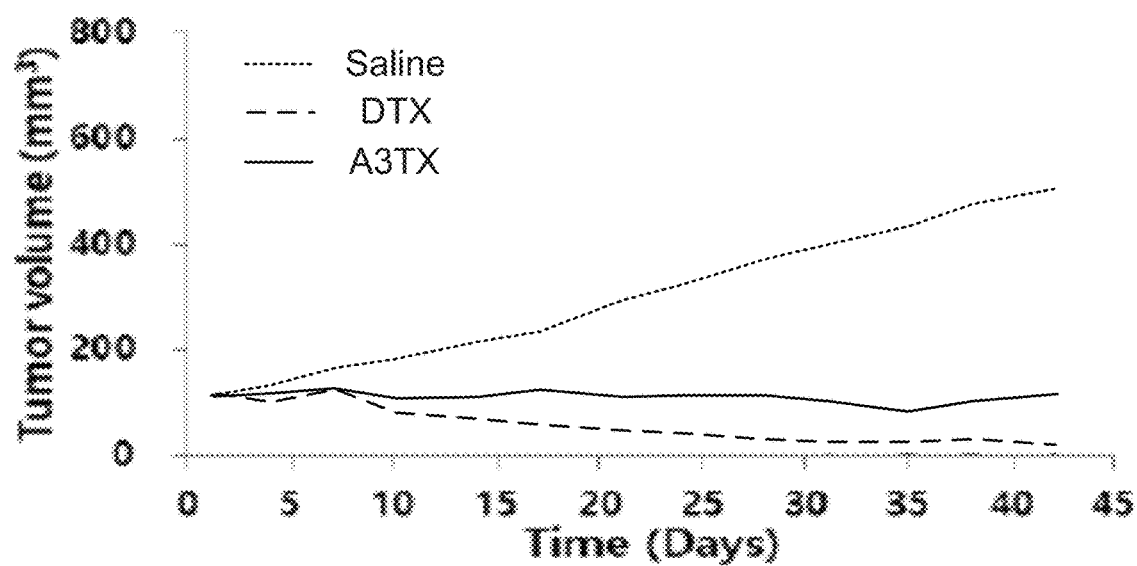
FIGS. 6A and 6B show the anticancer efficacy result of the A3Tx in the animal experiment (i.e., the mouse xenograft model) in accordance with one implementation of the present disclosure.
Figure 6B:
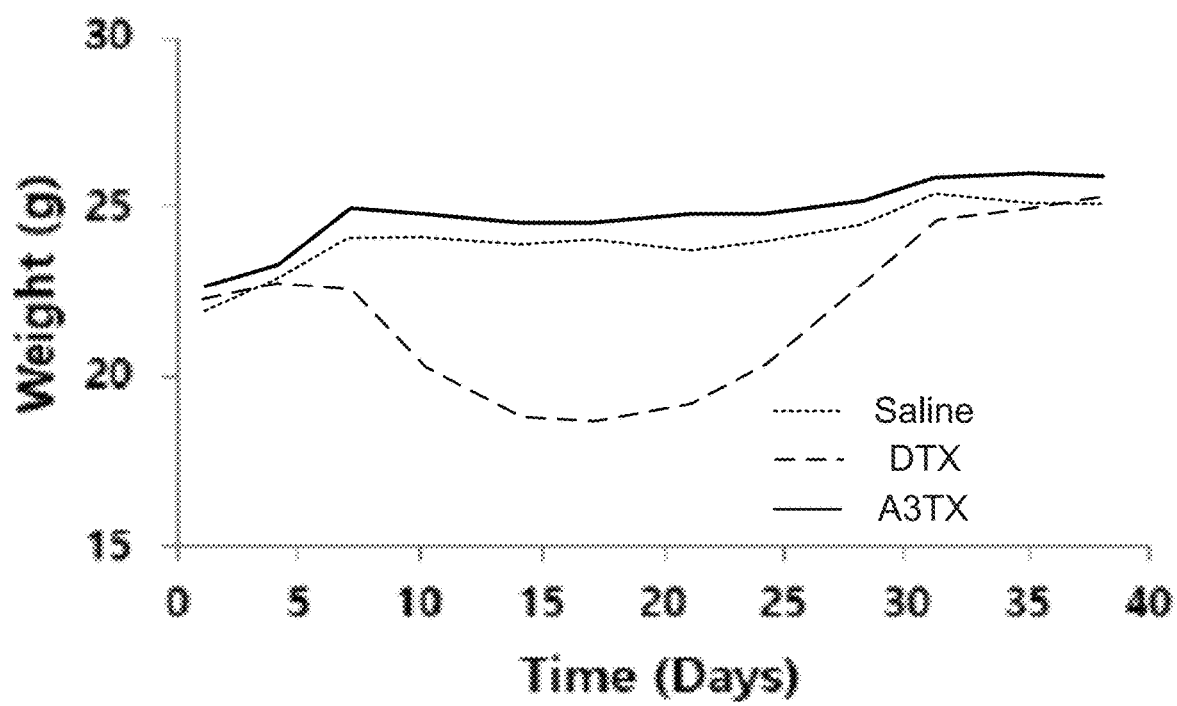

FIGS. 6A and 6B show the anticancer efficacy result of the A3Tx in the animal experiment (i.e., the mouse xenograft model) in accordance with one implementation of the present disclosure. The graphs show that A3Tx possesses the anti-cancer efficacy such as the starting material, docetaxel. Normally, non-treated group is injected with saline (NaCl solution) in anti-cancer efficacy study. A3Tx treatment group shows similar anticancer effects to docetaxel, and no weight loss was observed (dose: docetaxel standard, 20 mg/kg). Thus, the result of the animal experiment shows that A3Tx maintains the anticancer efficacy of docetaxel without the observed weight loss.

FIG. 6A shows that in PANC-1 model, A3Tx inhibited the tumor growth in terms of mean tumor volume. The rate of tumor growth was similar to that of DTX exhibiting no significant difference between the tumor volumes of A3Tx and DTX-treated group. Both DTX and A3Tx showed significant inhibition in tumor growth compared to negative control group (P<0.01).

The result of weight monitoring of A3Tx-treated group indicated no significant loss of body weight over time. Since body weight loss has been generally accepted as a sign of toxicity, this result confirms that A3Tx is a non-toxic anti-cancer drug at the test dose. However, in FIG. 5B, the significant body weight loss was observed in DTX-treated group from day 7 to day 24. As observed in the animal study, although DTX offers a clinical benefit of anti-cancer activity, it has a clear limitation such as weight loss. Taken together, Compared to DTX, A3Tx represents a good anti-cancer activity while having a negligible in vivo toxicity.

In one implementation, a compound useful as an anti-cancer drug is disclosed. The anti-cancer drug has the following formula:

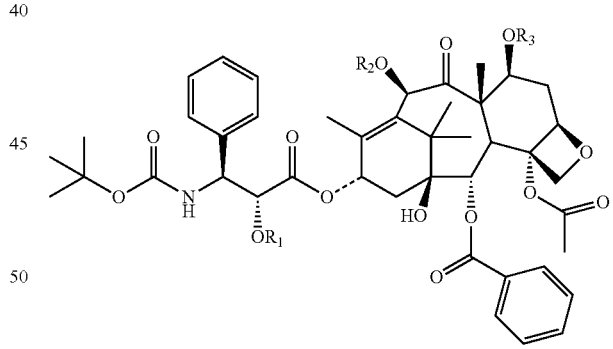

wherein $R_1=R_2=R_3=$aconitic anhydride has the following formula:

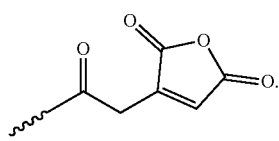

In another implementation, a method for synthesizing a docetaxel-aconitic anhydride conjugate using docetaxel is disclosed. The method includes: mixing aconitic anhydride with a chlorinating reagent to produce a first mixture; dissolving the first mixture in an organic solvent to produce a dissolved mixture; stirring the dissolved mixture; evaporating the organic solvent from the dissolved mixture to produce a second mixture; washing the second mixture with an impurity remover to remove impurities and to produce an aconitic anhydride chloride solution; and mixing the docetaxel with the produced aconitic anhydride chloride solution to produce the docetaxel-aconitic anhydride conjugate.

In one implementation, the docetaxel-aconitic anhydride conjugate has the following formula:

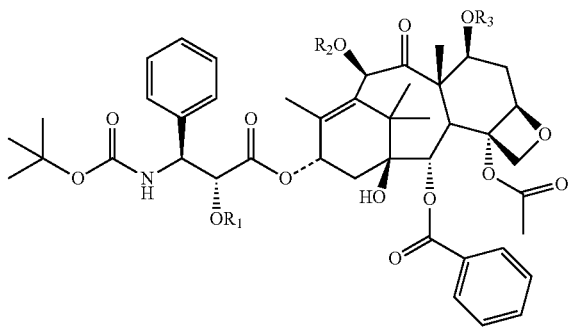

wherein $R_1=R_2=R_3=$aconitic anhydride having the following formula:

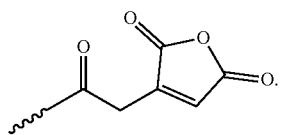

In one implementation, the chlorinating reagent includes phosphorus pentachloride. In one implementation, mixing the aconitic anhydride with the chlorinating reagent includes acylating the aconitic anhydride with the chlorinating reagent to prepare for acyl chloride derivative of aconitic anhydride. In one implementation, the acyl chloride derivative of aconitic anhydride includes aconitic anhydride chloride. In one implementation, the organic solvent includes methylene chloride. In one implementation, the dissolved mixture is stirred for approximately 1 to 2 hours. In one implementation, the organic solvent is evaporated using a rotary evaporator at room temperature. In one implementation, the impurity remover includes cyclohexane. In one implementation, the impurities are removed based on the solubility of the organic solvent. In one implementation, the method further includes dispersing the second mixture in cyclohexane. In one implementation, the method further includes centrifuging and decanting the cyclohexane to remove the impurities. In one implementation, the method further includes tri-substituting the docetaxel with the aconitic anhydride through chemical reaction with the aconitic anhydride chloride solution. In one implementation, the aconitic anhydride is directly conjugated to hydroxyl moieties of the docetaxel to produce the docetaxel-aconitic anhydride conjugate. In one implementation, the method further includes adding the produced aconitic anhydride chloride solution in methylene chloride or tetrahydrofuran. In one implementation, a molar ratio between the docetaxel and the aconitic anhydride chloride solution ranges from 1:3 to 1:10.

The description herein of the disclosed implementations is provided to enable any person skilled in the art to make or use the present disclosure. Numerous modifications to these implementations would be readily apparent to those skilled in the art, and the principals defined herein can be applied to other implementations without departing from the spirit or scope of the present disclosure. Thus, the present disclosure is not intended to be limited to the implementations shown herein but is to be accorded the widest scope consistent with the principal and novel features disclosed herein.

All features of each above-discussed example are not necessarily required in a particular implementation of the present disclosure. Further, it is to be understood that the description and drawings presented herein are representative of the subject matter which is broadly contemplated by the present disclosure. It is further understood that the scope of the present disclosure fully encompasses other implementations that may become obvious to those skilled in the art and that the scope of the present disclosure is accordingly limited by nothing other than the appended claims.

The invention claimed is:

1. A compound useful as an anti-cancer drug having the following formula:

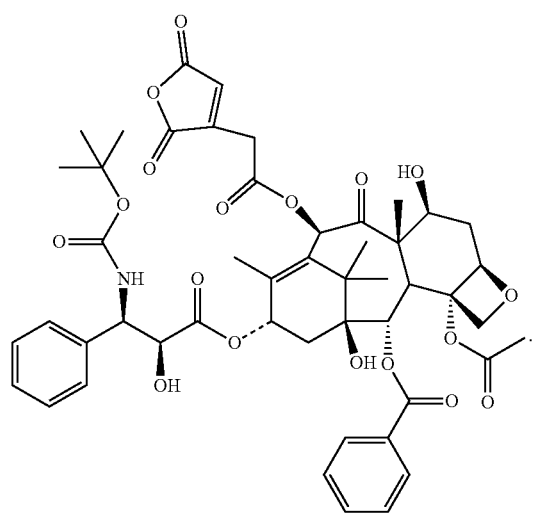

2. A method for synthesizing a docetaxel-aconitic anhydride conjugate using docetaxel, comprising:
mixing aconitic anhydride with a chlorinating reagent to produce a first mixture;
dissolving the first mixture in an organic solvent to produce a dissolved mixture;
stirring the dissolved mixture;
evaporating the organic solvent from the dissolved mixture to produce a second mixture;
washing the second mixture with an impurity remover to remove impurities and to produce an aconitic anhydride chloride solution; and
mixing the docetaxel with the produced aconitic anhydride chloride solution to produce the docetaxel-aconitic anhydride conjugate, by controlling the produced aconitic anhydride chloride to bind to a hydroxyl group of the docetaxel over at least one other hydroxyl group, wherein the produced docetaxel-aconitic anhydride conjugate has the following formula:

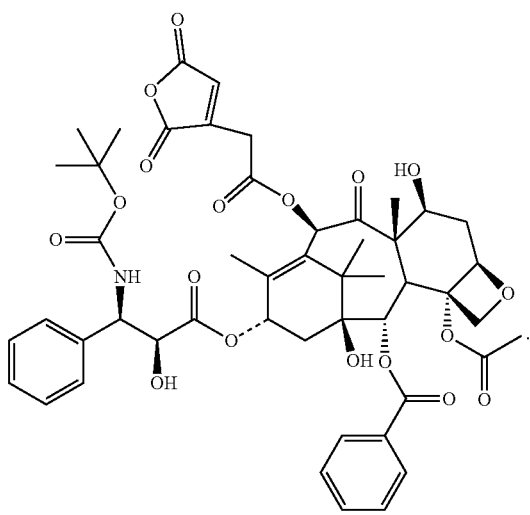

3. The method of claim 2, wherein the controlling the produced aconitic anhydride chloride to bind to the hydroxyl group of the docetaxel over the at least one other hydroxyl group is by adding a protective group to the at least one other hydroxyl group.

4. The method of claim 2, wherein the chlorinating reagent is phosphorus pentachloride.

5. The method of claim 2, wherein mixing the aconitic anhydride with the chlorinating reagent comprises
activating the aconitic anhydride with the chlorinating reagent to produce cis-aconitic anhydride.

6. The method of claim 5, wherein dissolving the first mixture in the organic solvent comprises
dissolving the cis-aconitic anhydride and the chlorinating reagent in methylene chloride.

7. The method of claim 2, wherein evaporating the organic solvent from the dissolved mixture to produce the second mixture comprises
evaporating the organic solvent from the dissolved mixture to produce cis-aconitic anhydride chloride.

8. The method of claim 2, further comprising
protecting the at least one other hydroxyl group of the docetaxel using trimethylsilyl chloride.

9. The method of claim 8, wherein the docetaxel comprises the hydroxyl group and the at least one other hydroxyl group as in the following formula:

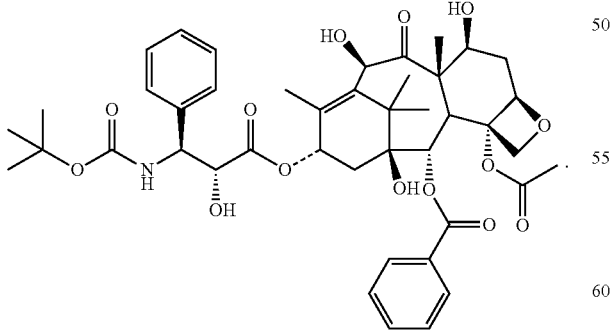

10. The method of claim 3, wherein the protective group is a trimethylsilyl chloride having the following formula:

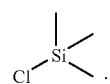

11. The method of claim 8, wherein mixing the docetaxel with the produced aconitic anhydride chloride solution comprises
mixing the protected docetaxel with cis-aconitic anhydride chloride in tetrahydrofuran (THF) as solvent to produce the docetaxel-aconitic anhydride conjugate.

12. The method of claim 11, further comprising:
stirring and washing the docetaxel-aconitic anhydride conjugate with ether; and
drying the washed docetaxel-aconitic anhydride conjugate to produce a disilyl-protected docetaxel-aconitic anhydride conjugate.

13. The method of claim 3, wherein the docetaxel added with the protected group has the following formula:

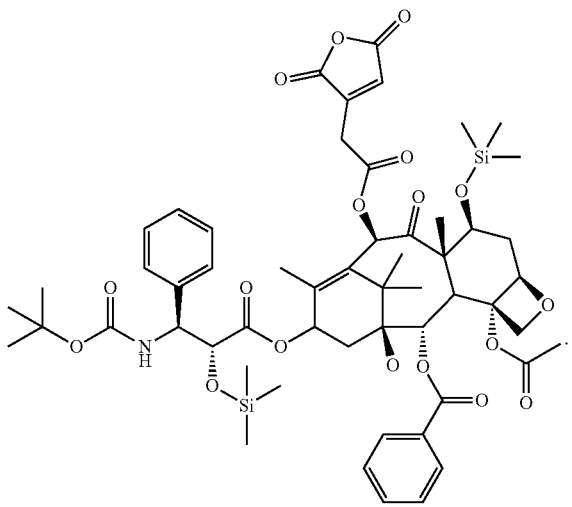 [SMILES: CC(=O)O[C@@]12CO[C@@H]1C[C@H](O[Si](C)(C)C)[C@@]1(C)C(=O)[C@H](OC(=O)CC3=CC(=O)OC3=O)C3=C(C)C(OC(=O)[C@H](O[Si](C)(C)C)[C@@H](NC(=O)OC(C)(C)C)c4ccccc4)C[C@@](O)([C@@H](OC(=O)c4ccccc4)C12)C3(C)C]

* * * * *